US011696885B2

(12) United States Patent
Lu et al.

(10) Patent No.: US 11,696,885 B2
(45) Date of Patent: Jul. 11, 2023

(54) RHAMNOLIPID DERIVATIVES AS EMULSIFIERS AND DISPERSING AIDS

(71) Applicant: Evonik Operations GmbH, Essen (DE)

(72) Inventors: Xin Lu, Essen (DE); Sandra Nattland, Essen (DE); Achim Friedrich, Hattingen (DE); Hans Henning Wenk, Mülheim an der Ruhr (DE)

(73) Assignee: Evonik Operations GmbH, Essen (DE)

( * ) Notice: Subject to any disclaimer, the term of this patent is extended or adjusted under 35 U.S.C. 154(b) by 160 days.

(21) Appl. No.: 16/631,248

(22) PCT Filed: Aug. 14, 2018

(86) PCT No.: PCT/EP2018/071974
§ 371 (c)(1),
(2) Date: Jan. 15, 2020

(87) PCT Pub. No.: WO2019/038125
PCT Pub. Date: Feb. 28, 2019

(65) Prior Publication Data
US 2020/0214959 A1 Jul. 9, 2020

(30) Foreign Application Priority Data
Aug. 24, 2017 (EP) .................... 17187675

(51) Int. Cl.
| | | |
|---|---|---|
| *A61Q 1/00* | (2006.01) | |
| *A61Q 19/00* | (2006.01) | |
| *A61Q 17/04* | (2006.01) | |
| *A61Q 19/10* | (2006.01) | |
| *A61K 8/04* | (2006.01) | |
| *A61K 8/60* | (2006.01) | |
| *A61K 8/06* | (2006.01) | |
| *A61K 8/92* | (2006.01) | |

(52) U.S. Cl.
CPC ............... *A61K 8/604* (2013.01); *A61K 8/06* (2013.01); *A61K 8/92* (2013.01); *A61Q 17/04* (2013.01); *A61Q 19/007* (2013.01); *A61Q 19/10* (2013.01)

(58) Field of Classification Search
CPC . A61K 8/604; A61K 8/06; A61K 8/92; A61Q 17/04; A61Q 19/007; A61Q 19/10
See application file for complete search history.

(56) References Cited

U.S. PATENT DOCUMENTS

| | | | |
|---|---|---|---|
| 5,989,568 A * | 11/1999 | Breton | |
| 7,129,218 B2 * | 10/2006 | Stipcevic | |
| 9,005,928 B2 | 4/2015 | Schaffer et al. | |
| 9,580,720 B2 | 2/2017 | Schaffer et al. | |
| 9,776,951 B2 | 10/2017 | Friedrich et al. | |
| 10,292,925 B2 | 5/2019 | Gu et al. | |
| 2004/0161444 A1 * | 8/2004 | Song | |
| 2014/0296168 A1 | 10/2014 | Schilling et al. | |
| 2017/0202770 A1 | 7/2017 | Friedrich et al. | |
| 2017/0306264 A1 | 10/2017 | Peggau et al. | |
| 2017/0335238 A1 | 11/2017 | Schilling et al. | |
| 2018/0016525 A1 | 1/2018 | Scheuermann et al. | |
| 2018/0023040 A1 | 1/2018 | Schilling et al. | |
| 2018/0344602 A1 | 12/2018 | Schuch et al. | |
| 2019/0040095 A1 | 2/2019 | Lu et al. | |
| 2019/0135734 A1 | 5/2019 | Liebig et al. | |
| 2019/0202771 A1 | 7/2019 | Von Hof et al. | |
| 2019/0269158 A1 | 9/2019 | Schilling et al. | |
| 2019/0300728 A1 | 10/2019 | Klostermann et al. | |
| 2019/0300917 A1 | 10/2019 | Eckstein et al. | |
| 2019/0307657 A1 | 10/2019 | Wenk et al. | |

FOREIGN PATENT DOCUMENTS

| | | |
|---|---|---|
| EP | 1889623 A2 | 2/2008 |
| EP | 3023431 A1 | 5/2016 |
| WO | 2001010447 A1 | 2/2001 |
| WO | 2012013554 A1 | 2/2012 |

OTHER PUBLICATIONS

Fisher (Journal of Food Science, published 1985, pp. 1-4) (Year: 1985).*
English International Search Report dated Sep. 26, 2018 in PCT/EP2018/071974 (3 pages).
German International Search Report dated Sep. 26, 2018 in PCT/EP2018/071974 (4 pages).
German Written Opinion dated Sep. 26, 2018 in PCT/EP2018/071974 (6 pages).

* cited by examiner

*Primary Examiner* — Alma Pipic
(74) *Attorney, Agent, or Firm* — Grüneberg and Myers PLLC

(57) ABSTRACT

The invention relates to a dispersion containing at least one rhamnolipid derivative and also to the use of the rhamnolipid derivatives as emulsifier or dispersing aid.

23 Claims, No Drawings

RHAMNOLIPID DERIVATIVES AS EMULSIFIERS AND DISPERSING AIDS

CROSS REFERENCE TO RELATED APPLICATIONS

This application is a 35 U.S.C. § 371 U.S. national phase entry of International Application No. PCT/EP2018/071974 having an international filing date of Aug. 14, 2018, which claims the benefit of European Application No. 17187675.8 filed Aug. 24, 2017, each of which is incorporated herein by reference in its entirety.

FIELD

The invention relates to a dispersion, in particular an emulsion, containing at least one rhamnolipid derivative and also to the use of the rhamnolipid derivatives as emulsifier or dispersing aid.

BACKGROUND

Rhamnolipids are surfactants which can be prepared by means of fermentation. They are composed of one to two rhamnose units and one to three, mostly β-hydroxy fatty acids. The fatty acids can be saturated or unsaturated.

The variation in the chain length and amount (congener) of the fatty acid portions has been described in a number of publications. (Howe et al., FEBS J. 2006; 273(22):5101-12; Abdel-Mawgoud et al., Appl Microbiol Biotechnol, 86, 2010; pp. 1323-1336). Few covalent derivatives of the fatty acid portions of rhamnolipids are known.

Miao et al., Journal of Surfactants and Detergents, 17 (6), 2014; 1069-1080, describes the synthesis of di-rhamnolipid ethyl esters by esterification with ethanol and also the suitability of the esters as nonionic surfactant.

WO2001010447 and EP1889623 disclose the pharmaceutical and cosmetic applications of rhamnolipids and short-chain rhamnolipid esters (C1-C6; methyl to hexyl esters, linear or branched), in particular in wound healing.

SUMMARY

It is an object of the invention to provide excellent emulsifiers or dispersing aids.

DETAILED DESCRIPTION

It was found that, surprisingly, the rhamnolipid derivatives described below, which are derivatized by a relatively long carbon chain or by substituents having in total a relatively large number of carbon atoms, have outstanding emulsifying and dispersing abilities.

The present invention therefore provides a dispersion containing at least one rhamnolipid derivative as described in claim 1.

The invention further provides for the use of these rhamnolipid derivatives as emulsifier or dispersing aid.

An advantage of the rhamnolipid derivatives used in the present invention is their good biodegradability.

A further advantage of the present invention is based on the fact that the rhamnolipid derivatives can be incorporated into the emulsion via the water phase.

A further advantage of the present invention is the low skin-irritant effect of the rhamnolipid derivatives used.

A further advantage of the present invention is the low eye-irritant effect of the rhamnolipid derivatives used.

A further advantage of the present invention is the good dispersing action of the rhamnolipid derivatives used with respect to decorative pigments, and the high colorfastness of, e.g., make-up products, which can be achieved thereby.

A further advantage of the present invention is the good emulsifying action with respect to organic UV filters, or the good dispersing action with regard to inorganic UV filters.

A further advantage of the present invention is that following application of the inventive emulsions the skin is less severely defatted.

A further advantage of the present invention is that the inventive emulsions can eliminate undesired odors from skin.

A further advantage of the present invention is that the inventive emulsions can improve the skin elasticity.

A further advantage of the present invention is that the inventive emulsions are rapidly absorbed into the skin and leave a light and pleasant skin feel.

A further advantage of the present invention is that emulsions with low viscosities can be produced.

A further advantage of the present invention is that the inventive emulsions improve skin moisture.

A further advantage of the present invention is that the inventive emulsions have good foamability in combination with further surfactants or non-derivatized mono- or di-rhamnolipids.

A further advantage of the present invention is that the rhamnolipid derivatives can also be used as coemulsifiers in water-in-oil emulsions.

The terms "rhamnolipid" and "rhamnolipid ester" in connection with the present invention also always include their corresponding salts.

The terms "rhamnolipid" and "rhamnolipid amide" in connection with the present invention also always include their corresponding salts.

The term "mono-rhamnolipid" in connection with the present invention is understood as meaning compounds of the general formula (I) shown below, where $R^3$=H or salts thereof, in which n=0.

Distinct rhamnolipids are abbreviated according to the following nomenclature: "diRL-CXCY" is understood as meaning di-rhamnolipids of the general formula (I) where $R^3$=H or salts thereof, in which one of the radicals $R^1$ and $R^2$=(CH$_2$)$_o$—CH$_3$ where o=X-4 and the remaining radical $R^1$ or $R^2$=(CH$_2$)$_o$—CH$_3$ where o=Y-4.

"monoRL-CXCY" is understood as meaning mono-rhamnolipids of the general formula (I) where $R^3$=H or salts thereof, in which one of the radicals $R^1$ and $R^2$=(CH$_2$)$_o$—CH$_3$ where o=X-4 and the remaining radical $R^1$ or $R^2$=(CH$_2$)$_o$—CH$_3$ where o=Y-4.

The nomenclature used therefore does not distinguish between "CXCY" and "CYCX". For rhamnolipids where m=0, monoRL-CX or diRL-CX is used accordingly.

If one of the abovementioned indices X and/or Y is provided with ":Z", this signifies that the respective radical $R^1$ and/or $R^2$=an unbranched, unsubstituted hydrocarbon radical having X-3 or Y-3 carbon atoms having Z double bonds.

Analogous nomenclature is used for rhamnolipid esters in the form di/monoRL-CXCY:Z esters.

The "pH" in connection with the present invention is defined as the value which is measured for the corresponding substance at 25° C. after stirring for 5 minutes using a pH electrode calibrated in accordance with ISO 4319 (1977).

Unless stated otherwise, all percentages (%) given are percentages by mass.

The present invention provides a dispersion containing at least A) one rhamnolipid derivative selected from the group consisting of rhamnolipid ester of the general formula (I) and rhamnolipid amide of the general formula (II)

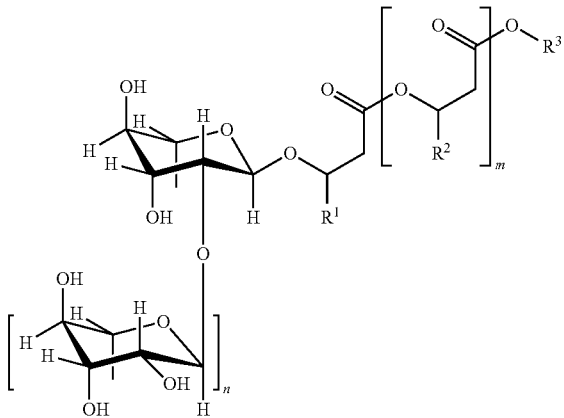

general formula (I),
where
m=2, 1 or 0, in particular 1 or 0,
n=1 or 0, in particular 1,
$R^1$=organic radical having 2 to 24, preferably 5 to 13, carbon atoms, in particular optionally branched, optionally substituted, in particular hydroxy-substituted, optionally unsaturated, in particular optionally mono-, bi- or tri-unsaturated, alkyl radical, preferably one selected from the group consisting of pentenyl, heptenyl, nonenyl, undecenyl and tridecenyl and $(CH_2)_o$—$CH_3$ where o=1 to 23, preferably 4 to 12,
$R^2$=independently of one another, identical or different, organic radical having 2 to 24, preferably 5 to 13, carbon atoms, in particular optionally branched, optionally substituted, in particular hydroxy-substituted, optionally unsaturated, in particular optionally mono-, bi- or tri-unsaturated, alkyl radical, preferably one selected from the group consisting of pentenyl, heptenyl, nonenyl, undecenyl and tridecenyl and $(CH_2)_o$—$CH_3$ where o=1 to 23, preferably 4 to 12, and
$R^3$=aliphatic radical having 7 to 32 carbon atoms, preferably 8 to 24 carbon atoms, particularly preferably 10 to 22 carbon atoms,

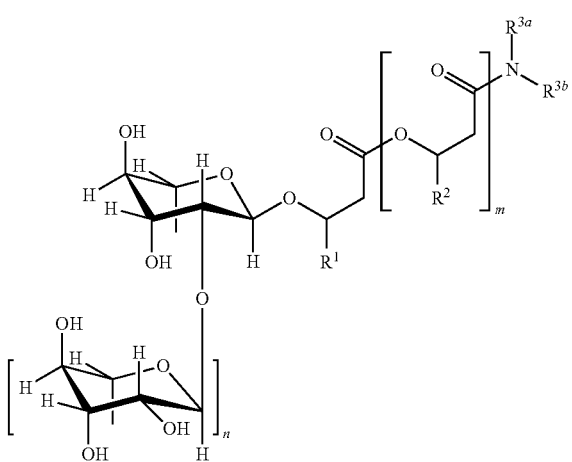

general formula (II),
where
m=2, 1 or 0, in particular 1 or 0,
n=1 or 0, in particular 1,
$R^1$=organic radical having 2 to 24, preferably 5 to 13, carbon atoms, in particular optionally branched, optionally substituted, in particular hydroxy-substituted, optionally unsaturated, in particular optionally mono-, bi- or tri-unsaturated, alkyl radical, preferably one selected from the group consisting of pentenyl, heptenyl, nonenyl, undecenyl and tridecenyl and $(CH_2)_o$—$CH_3$ where o=1 to 23, preferably 4 to 12,
$R^2$=independently of one another, identical or different, organic radical having 2 to 24, preferably 5 to 13, carbon atoms, in particular optionally branched, optionally substituted, in particular hydroxy-substituted, optionally unsaturated, in particular optionally mono-, bi- or tri-unsaturated, alkyl radical, preferably one selected from the group consisting of pentenyl, heptenyl, nonenyl, undecenyl and tridecenyl and $(CH_2)_o$—$CH_3$ where o=1 to 23, preferably 4 to 12,
$R^{3a}$=organic radical having 1 to 32, preferably 8 to 24, particularly preferably 10 to 22, carbon atoms,
and $R^{3b}$=organic radical having 1 to 32, preferably 8 to 24, particularly preferably 10 to 22, carbon atoms or H, preferably H,
with the proviso that the sum of the carbon atoms present in $R^{3a}$ and $R^{3b}$ is 7 to 44, preferably 8 to 24, particularly preferably 10 to 22.

According to the invention, the rhamnolipid derivative is preferably present in the continuous phase of the inventive dispersion.

Rhamnolipid esters likewise particularly preferably present according to the invention are selected from diRLC10C10 esters, diRLC8C10 esters, diRLC10C12 esters, diRLC10C12:1 esters and monoRLC10C10 esters where $R^3$=aliphatic radical having 7 to 32 carbon atoms, preferably 8 to 24 carbon atoms, particularly preferably 10 to 22 carbon atoms.

Rhamnolipid esters particularly preferably present according to the invention are characterized in that $R^3$ is selected from the group of the $R^3$ radicals directly derived from $R^3OH$=natural fatty alcohol.

In this connection, in particular rhamnolipid esters are preferably selected according to the invention from diRLC10C10 esters, diRLC8C10 esters, diRLC10C12 esters, diRLC10C12:1 esters and monoRLC10C10 esters.

In connection with the present invention, the term "natural fatty alcohol" is understood to mean the alcohols which can be obtained by reduction of natural triacylglycerols, fatty acids or fatty acid methyl esters; these comprise in particular linear, saturated or unsaturated primary alkan-1-ol s with 8-32 carbon atoms.

Rhamnolipid esters very particularly preferably present according to the invention are characterized in that $R^3$ is selected from branched or linear alkyl radicals, preferably with 8 to 24, in particular 10 to 22, carbon atoms. In this connection, in particular rhamnolipid esters are preferably selected from diRLC10C10 esters, diRLC8C10 esters, diRLC10C12 esters, diRLC10C12:1 esters and monoRLC10C10 esters.

Rhamnolipid esters very particularly preferably present according to the invention are characterized in that $R^3$ is selected from the group comprising, preferably consisting of, lauryl, myristyl, palmityl, stearyl, arachidyl and behenyl radicals. In this connection, in particular rhamnolipid esters are preferably selected according to the invention from diRLC10C10 esters, diRLC8C10 esters, diRLC10C12 esters, diRLC10C12:1 esters and monoRLC10C10 esters. The rhamnolipid esters present according to the invention are preferably mixture compositions of rhamnolipid esters which are characterized in particular in that they contain mono- and di-rhamnolipid esters.

Depending on the application, it may be preferred that the mixture compositions present according to the invention comprise more percent by weight of mono-rhamnolipid esters than di-rhamnolipid esters or more percent by weight of di-rhamnolipid esters than mono-rhamnolipid esters, where the percentages by weight refer to all of the mono- and di-rhamnolipid esters present in the mixture composition.

Thus, for example, the mixture compositions present according to the invention can comprise, for example, more than 60 wt %, in particular more than 80 wt %, or even more than 95 wt %, of di-rhamnolipid esters, or else also, for example, more than 60 wt %, in particular more than 80 wt %, or even more than 95 wt %, of mono-rhamnolipid esters, where the percentages by weight refer to all of the mono- and di-rhamnolipid esters present in the mixture composition.

The rhamnolipid esters present according to the invention may be prepared by a process comprising the process steps
A) providing at least one rhamnolipid,
B) reacting the rhamnolipid with at least one coupling reagent,
C) reacting the rhamnolipid activated by process step B) with an alcohol having 1 to 32, in particular 3 to 32, carbon atoms, and optionally
D) purifying the rhamnolipid ester.

Process step A) is carried out according to the generally known processes of the prior art, in particular using genetically modified microorganisms which preferably overexpress rhamnolipid synthesis genes, these genes preferably being selected from rhlA, rhlB and rhlC. Corresponding instructions can be found by the person skilled in the art in e.g. US2014296168 and WO2012013554.

In process step B), for example dicyclohexylcarbodiimide, diisopropylcarbodiimide, 1-(3-dimethylaminopropyl)-3-ethylcarbodiimide hydrochloride, N-cyclohexyl-N'-(2'-morpholinoethyl)carbodiimide metho-p-toluenesulfonate, N-benzyl-N'-3'-dimethylaminopropylcarbodiimide hydrochloride, 1-ethyl-3-(3-dimethylaminopropyl)carbodiimide-N-ethylcarbodiimide hydrochloride or carbonyldiimidazole may be used as coupling reagent.

Rhamnolipid amides preferably present according to the invention are selected from those compounds of the general formula (II) in which organic radicals $R^{3a}$ and $R^{3b}$ are selected from optionally mono- or polyunsaturated alkyl radicals which optionally have at least one amine group.

Rhamnolipid amides particularly preferably present are selected from compounds of the general formula (II), where
m=2, 1 or 0, in particular 1 or 0,
n=1 or 0, in particular 1,
$R^1$=optionally branched, optionally substituted, in particular hydroxy-substituted, optionally unsaturated, in particular optionally mono-, bi- or tri-unsaturated, alkyl radical, with 2 to 24, preferably 5 to 13, carbon atoms, preferably one selected from the group consisting of pentenyl, heptenyl, nonenyl, undecenyl and tridecenyl and $(CH_2)_o$—$CH_3$ where o=1 to 23, preferably 4 to 12,
$R^2$=optionally branched, optionally substituted, in particular hydroxy-substituted, optionally unsaturated, in particular optionally mono-, bi- or tri-unsaturated, alkyl radical, with 2 to 24, preferably 5 to 13, carbon atoms, preferably one selected from the group consisting of pentenyl, heptenyl, nonenyl, undecenyl and tridecenyl and $(CH_2)_o$—$CH_3$ where o=1 to 23, preferably 4 to 12.

Rhamnolipid amides preferably present are selected from compounds of the general formula (II), where $R^{3a}$ is selected from the group of the alkyl radicals which optionally have amine groups, and $R^{3b}$=organic radical with 1 to 8 carbon atoms, in particular alkyl radical, or H, particularly preferably H.

Rhamnolipid amides preferably present are selected from diRLC10C10 amides, diC8C10 amides, diRLC10C12 amides, diRLC10C12:1 amides and also monoRLC10C10 amides where $R^{3a}$=organic radical with 8 to 24, preferably 10 to 22, carbon atoms, in particular alkyl radical, and preferably $R^{3b}$=H.

In an alternative preferred embodiment, the rhamnolipid amides present are selected from compounds of the general formula (II), where
$R^{3a}$=organic radical with 10 to 32 carbon atoms, in particular alkyl radical,
and $R^{3b}$=organic radical with 10 to 32 carbon atoms, in particular alkyl radical,
where it is in particular preferred that $R^{3a}$ and $R^{3b}$ are independently of one another selected from alkyl radicals with 10 to 22 carbon atoms.

In this connection, in particular rhamnolipid amides are preferably selected from diRLC10C10 amides, diRLC8C10 amides, diRLC10C12 amides, diRLC10C12:1 amides and monoRLC10C10 amides.

Very particularly preferred rhamnolipid amides are characterized in that $R^{3a}$ is selected from the group comprising, preferably consisting of,

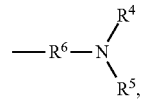

where
$R^4$ and $R^5$=independently of one another, identical or different alkyl radical with 1 to 6, preferably 1 to 3, particularly preferably 1, carbon atom(s),
$R^6$=an alkylene group with 1 to 6, preferably 2 to 3, carbon atoms,
and

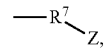

where
$R^7$=an alkylene group with 1 to 22, preferably 2 to 18, in particular 3 to 8, carbon atoms,
Z=H, OH, $OR^8$, where
$R^8$=alkyl radical with 1 to 6, preferably 1 to 3, particularly preferably 1, carbon atom(s), and preferably
$R^{3b}$=H.

In this connection, in particular rhamnolipid amides are preferably selected from diRLC10C10 amides, diRLC8C10 amides, diRLC10C12 amides, diRLC10C12:1 amides and monoRLC10C10 amides.

In an alternative preferred embodiment, the rhamnolipid amides present according to the invention are characterized in that the radical —$NR^{3a}R^{3b}$ is derived from an amine $NHR^{3a}R^{3b}$, selected from amino acids and peptides. Amino acids preferred in this connection are selected from the proteinogenic amino acids. Peptides further preferred in this connection are selected from peptides consisting of proteinogenic amino acids, in particular those peptides comprising 2 to 20, in particular 4 to 16, very particularly preferably 4 to 8, amino acids.

The rhamnolipid amides present according to the invention are preferably mixture compositions of rhamnolipid amides which are characterized in particular in that they contain mono- and di-rhamnolipid amides.

Depending on the application, it may be preferred that the mixture compositions present according to the invention comprise more percent by weight of mono-rhamnolipid amides than di-rhamnolipid amides or more percent by weight of di-rhamnolipid amides than mono-rhamnolipid amides, where the percentages by weight refer to all of the mono- and di-rhamnolipid amides present in the mixture composition.

Thus, for example, the mixture compositions present according to the invention can comprise, for example, more than 60 wt %, in particular more than 80 wt %, or even more than 95 wt %, of di-rhamnolipid amides, or else also, for example, more than 60 wt %, in particular more than 80 wt %, or even more than 95 wt %, of mono-rhamnolipid amides, where the percentages by weight refer to all of the mono- and di-rhamnolipid amides present in the mixture composition.

The rhamnolipid amides present according to the invention may be obtained by a process comprising the process steps
A) providing at least one rhamnolipid,
B) reacting the rhamnolipid with at least one coupling reagent,
C) reacting the rhamnolipid activated by process step B) with an amine, and optionally
D) purifying the rhamnolipid amide.

Process step A) is carried out according to the generally known processes of the prior art, in particular using genetically modified microorganisms which preferably overexpress rhamnolipid synthesis genes, these genes preferably being selected from rhlA, rhlB and rhlC. Corresponding instructions can be found by the person skilled in the art in e.g. US2014296168 and WO2012013554.

In process step B), for example dicyclohexylcarbodiimide, diisopropylcarbodiimide, 1-(3-dimethylaminopropyl)-3-ethylcarbodiimide hydrochloride, N-cyclohexyl-N'-(2'-morpholinoethyl)carbodiimide metho-p-toluenesulfonate, N-benzyl-N'-3'-dimethylaminopropylcarbodiimide hydrochloride, 1-ethyl-3-(3-dimethylaminopropyl)carbodiimide-N-ethylcarbodiimide hydrochloride and carbonyldiimidazole may be used as coupling reagent.

In process step C), a catalyst such as, for example, N-ethyldiisopropylamine, trialkylamine, pyridine, 4-dimethylaminopyridine and hydroxybenzotriazole may be used.

Dispersions preferred according to the invention are characterized in that they are an emulsion, in particular an oil-in-water emulsion.

Dispersions preferred according to the invention are characterized in that they contain
A) the rhamnolipid derivative,
B) at least one cosmetic oil, and
C) water.
Component B) is a cosmetic oil.

In connection with the present invention, the term "cosmetic oil" is understood to mean water-immiscible liquids suitable for the production of cosmetic formulations. In the context of the present invention, water-immiscible signifies that, at room temperature, aqueous mixtures of cosmetic oils at oil concentrations of 0.5-99.5 vol %, based on the total mixture, result in cloudiness visible to the human eye or in the formation of two or more phases. In the context of the present invention, furthermore, cosmetic oils are preferably characterized in that they have an interfacial tension with respect to water of >5 mN/m. Cosmetic oils can be for example oleochemistry-based or silicone chemistry-based.

Preferably according to the invention, the inventive dispersion contains cosmetic oils selected from the group of the fatty alcohols, esters of linear fatty acids with linear or branched fatty alcohols, esters of branched fatty acids with linear or branched fatty alcohols, esters of linear fatty acids with unbranched or branched polyhydric alcohols, esters of branched fatty acids with unbranched or branched polyhydric alcohols, esters of linear fatty acids with unbranched or branched alcohols, esters of branched fatty acids with unbranched or branched alcohols, esters of alkylhydroxycarboxylic acids with linear or branched fatty alcohols. In addition, mono-, di- or triglycerides in liquid or solid form. In addition, esters of carboxylic acids, aromatic carboxylic acids or dicarboxylic acids with linear or branched fatty alcohols, unbranched or branched polyhydric alcohols or unbranched or branched alcohols. In addition, linear, cyclic or branched hydrocarbons, with or without substituents, with or without double bonds. In addition, vegetable oils, carbonates with unbranched or branched alcohols, carbonates with unbranched or branched polyhydric alcohols, carbonates with linear or branched fatty alcohols. In addition, ethers with or without alkoxy groups, or silicone oils with or without organic modification. In addition, mixtures of these oils in any ratios. Preferably, esters of linear fatty acids with linear or branched fatty alcohols, esters of branched fatty acids with linear or branched fatty alcohols, esters of linear fatty acids with unbranched or branched polyhydric alcohols, esters of branched fatty acids with unbranched or branched polyhydric alcohols, esters of linear fatty acids with unbranched or branched alcohols, esters of branched fatty acids with unbranched or branched alcohols. In addition, mono-, di- or triglycerides in liquid or solid form. In addition, esters of carboxylic acids, aromatic carboxylic acids or dicarboxylic acids with linear or branched fatty alcohols, unbranched or branched polyhydric alcohols or unbranched or branched alcohols. In addition, linear, cyclic or branched hydrocarbons, with or without substituents, with or without double bonds. In addition, vegetable oils, carbonates with unbranched or branched alcohols, carbonates with unbranched or branched polyhydric alcohols, carbonates with linear or branched fatty alcohols, more preferably linear, cyclic or branched hydrocarbons, with or without substituents, with or without double bonds. In addition, carbonates with unbranched or branched alcohols, carbonates with unbranched or branched polyhydric alcohols, carbonates with linear or branched fatty alcohols. Esters of branched fatty acids with unbranched or branched polyhydric alcohols.

Emulsions preferred according to the invention are characterized in that they contain
A) at least one rhamnolipid derivative in an amount of 0.1 wt % to 10.0 wt %, preferably in an amount of 0.5 wt % to 7.0 wt %, more preferably in an amount of 1.0 wt % to 5.0 wt %,
B) the oil phase in an amount of 5.0 wt % to 79.9 wt %, preferably in an amount of 10.0 wt % to 50.0 wt %, more preferably in an amount of 12.0 wt % to 35.0 wt %, C) the water phase in an amount of 20.0 wt % to 94.9 wt %, preferably in an amount of 50.0 wt % to 90.0 wt %, more preferably in an amount of 65.0 wt % to 88.0 wt %, where the percentages by weight refer to the total emulsion.

The present invention further provides for the use of the rhamnolipid derivatives present in the inventive dispersions as emulsifier or dispersing aid. In the context of the present invention, the rhamnolipid derivatives preferably present in the inventive dispersions are preferably used as emulsifier or dispersing aid.

The examples adduced hereinafter describe the present invention by way of example, without any intention that the invention, the scope of application of which is apparent from the entirety of the description and the claims, be restricted to the embodiments specified in the examples.

EXAMPLES

Example 1: Production of Di-Rhamnolipids

A fermentation with a recombinant strain *Pseudomonas putida* KT2440S pBBR1MCS2-Plac-rhlABC-T-Ptac-rhlC-T was carried out. The construction of the strain is described in US2014296168. The preculture in the shake flask was carried out as described in WO2012013554. For the main culture, a mineral medium (M9) was likewise used. The fermentation takes place in a glucose-limited fed-batch process in a 2 litre fermenter. The feeding in of glucose is regulated by reference to the dissolved-oxygen signal. The partial pressure of oxygen in the fermentation broth was regulated at 20% saturation via the stirrer speed. The pH is adjusted to 7 via a pH electrode and addition of 2 M sulfuric acid or of a 20% by weight ammonia solution. In order to prevent excessive foaming of the fermentation broth, the antifoam DOW Corning 1500 was metered in as required. The fermentation was conducted over 4 days to a dry biomass of 15 g/l. The rhamnolipid concentration was determined by HPLC and was 9.8 g/l. After separating off the cells by means of centrifugation at 10 000 g, the fermentation broth was adjusted to a pH of 3.1 by adding concentrated $H_2SO_4$. Renewed centrifugation at 10,000 g gave a pasty solid concentrate with an RL fraction of 45% by weight and with a viscosity of >10 000 mPas. With continuous stirring, a 50% by weight strength aqueous KOH solution was added to the pasty suspension of the concentrated rhamnolipid precipitate and a pH of 6 was established. The pasty mass liquefied at this point with an accompanying sharp drop in viscosity. The suspension gave rise to a clear solution. By adding water, the solution was adjusted to an active content of 35% by weight. The rhamnolipid purity was >90% by weight, based on the dry mass.

Rhamnolipid species detected by HPLC were:

| RL total [%] (HPLC) | 91 |
|---|---|
| diRL-C8C10 | 13.9 |
| monoRL-C8C10 | 0.51 |
| diRL-C10C10 | 61.4 |
| monoRL -C10C10 | 1.4 |
| diRL-C10C12:1 | 5.9 |
| diRL-C10C12 | 5.5 |
| other RL | 2.2 |

Example 2: Production of Mono-Rhamnolipids

The 35% by weight rhamnolipid solution prepared as described above was diluted to 1% by adding water. Two litres of this solution were heated to 50° C. With gentle stirring, 200 units of a thermostable rhamnosidase (ThermoActive™ Rhamnosidase A, Prokazyme) were added and the reaction was carried out overnight. After 20 h, a sample of the solution was analysed by means of HPLC. The di-rhamnolipid had been completely converted to mono-rhamnolipid and rhamnose. Then, the enzyme was inactivated at 80° C. for one hour. The entire mixture was then freeze-dried. The freeze-dried product was adjusted to a mono-rhamnolipid active content of 35% by weight by adding water.

Example 3a: Synthesis of Di-Rhamnolipid Behenyl Amide

To activate the acid function, 25 g of di-rhamnolipid (40 mmol) with 6.25 ml of diisopropylcarbodiimide (40 mmol) are dissolved in THF at 55° C. When an acid number of <2 is reached, 15.6 g (48 mmol) of behenyl amine are added, and also 1 wt % of 4-dimethylaminopyridine for the catalysis. The water of reaction formed promotes the formation of N,N'-diisopropylurea as secondary component. After a reaction time of 5 hours, the reaction mixture is dried on a rotary evaporator (45° C., <300 mbar); purification takes place by extraction through shaking with ethyl acetate (1): water (1) (2×20 ml in each case) in order to separate off the urea formed.

The ethyl acetate phase is evaporated (rotary evaporator, 45° C., <300 mbar) and the rhamnolipid behenyl amide remains as solid.

Further purification of the product can take place by means of column chromatography. For this, Silica 60 Gel (SIGMA Aldrich) serves as stationary phase and ethyl acetate (99): water (1) with 1% acetic acid serves as mobile phase. Behenyl amine residues, polar by-products or possible cleavage products are removed from a 5% strength solution of the crude product. For careful separation, a fraction comprises 10 ml at a dropping rate of 15 ml/min and a total volume of 200 ml of starting solution.

Example 3b: Synthesis of Mono-Rhamnolipid Dioctyl Amide

To activate the acid function, 20.2 g of mono-rhamnolipid (40 mmol) with 6.25 ml of diisopropylcarbodiimide are dissolved in toluene at 55° C. When the mixture reaches an acid number of <2, 9.66 g (40 mmol) of dioctyl amine are added, and also 1 wt % of 4-dimethylaminopyridine for the catalysis. Any unreacted coupling reagent should be deactivated beforehand by addition of 2 ml of water. After a reaction time of 10 h, work-up is carried out. The reaction mixture is dried on a rotary evaporator (45° C., <300 mbar). For purification, the crude product is dissolved in ethyl acetate (2 parts) and extracted through shaking with water (1 part) at pH 5.8. The rhamnolipid amide remains in the ethyl acetate phase. (filter off insoluble fractions). This is likewise dried on a rotary evaporator (45° C., <100 mbar), in order to retain the rhamnolipid amide.

Example 3c: Synthesis of Mono-Rhamnolipid Stearyl Amide

To activate the acid function, 20.2 g of mono-rhamnolipid (40 mmol) with 6.25 ml of diisopropylcarbodiimide are dissolved in THF at 55° C. When the mixture reaches an acid number of <2, 10.8 g (40 mmol) of octadecyl amine are added, and also 1 wt % of 4-dimethylaminopyridine for the catalysis. Any unreacted coupling reagent should be deactivated beforehand by addition of 2 ml of water. After a reaction time of 10 h, work-up is carried out. The reaction mixture is dried on a rotary evaporator (45° C., <300 mbar). For purification, the crude product is dissolved in ethyl acetate (2 parts) and extracted through shaking with water (1 part) at pH 5.8. The rhamnolipid amide remains in the ethyl acetate phase. (filter off insoluble fractions). This is likewise dried on a rotary evaporator (45° C., <100 mbar), in order to retain the rhamnolipid amide.

Example 4a: Synthesis of Di-Rhamnolipid Stearyl Ester

To activate the acid function, 25 g of di-rhamnolipid (40 mmol) from Example 1 with 6.25 ml of diisopropylcarbodiimide are dissolved in THF at 55° C. When the mixture achieves an acid number of <2, 10.8 g of stearyl alcohol (40 mmol) are added, as is 1 wt % of 4-dimethylaminopyridine for the catalysis. Any unreacted coupling reagent should be inactivated beforehand by adding 2 ml of water. After a reaction time of 10 h, work-up is carried out. The reaction mixture is dried on a rotary evaporator (45° C., <300 mbar); purification takes place by extraction through shaking with ethyl acetate (1): water (1) in two steps with 250 ml in each case. The rhamnolipid ester remains in the ethyl acetate phase. This is likewise dried on a rotary evaporator (45° C., <100 mbar); the viscous rhamnolipid ester remains.

Further purification of the product can take place by means of column chromatography. For this, Silica 60 Gel (SIGMA Aldrich) serves as stationary phase and ethyl acetate (99): water (1) with 1% acetic acid serves as mobile phase. Polar by-products or possible cleavage products are removed from a 5% strength solution of the rhamnolipid ester crude product. For careful separation, a fraction comprises 10 ml at a dropping rate of 15 ml/min and a total volume of 200 ml of starting solution.

Analytical determination by means of HPLC was carried out on a 50*3.0 mm column Poroshell 120 C18 (2.7 μm) in 20 mM $NH_4$ formate in $H_2O$ and MeCN at 30° C. for 35 min.

Example 4b: Synthesis of Mono-Rhamnolipid Stearyl Ester

To activate the acid function, 20.2 g of mono-rhamnolipid (40 mmol) with 6.25 ml of diisopropylcarbodiimide are dissolved in THF at 55° C. When the mixture reaches an acid number of <2, 10.8 g (40 mmol) of stearyl alcohol are added, and also 1 wt % of 4-dimethylaminopyridine for the catalysis. Any unreacted coupling reagent should be deactivated beforehand by addition of 2 ml of water. After a reaction time of 10 h, work-up is carried out. The reaction mixture is dried on a rotary evaporator (45° C., <300 mbar). For purification, the crude product is dissolved in ethyl acetate (2 parts) and extracted through shaking with water (1 part) at pH 5.8. The rhamnolipid ester remains in the ethyl acetate phase. (filter off insoluble fractions). This is likewise dried on a rotary evaporator (45° C., <100 mbar), in order to retain the viscous rhamnolipid ester.

Example 5a: Non-Inventive Synthesis of Di-Rhamnolipid Ethyl Esters

The synthesis was carried out according to the procedure from the paper by Miao et al., European Journal of Lipid Science and Technology, 117, 2015; 156-1609.

For this purpose, di-rhamnolipid from Example 1 was reacted with ethanol and sulfuric acid at 0° C. as described in the literature. The detected yield was less than 5%.

Inter alia, this can in particular be ascribed to the lack of coupling reagent.

Example 5b: Non-Inventive Synthesis of Mono-Rhamnolipid Ethyl Esters

The synthesis was carried out according to the procedure from the paper by Miao et al., European Journal of Lipid Science and Technology, 117, 2015; 156-1609.

For this purpose, mono-RL from Example 2 was stirred into ethanol at 0° C. and the esterification was catalyzed with sulfuric acid. The detected yield was also less than 5% in this case.

Example 6: Emulsifying Performance

All concentrations in the application examples are given in percent by weight. Customary homogenization processes known to those skilled in the art were used to produce the emulsions. The emulsions were therefore produced typically by heating oil phase and water phase to 70-75° C. Subsequently, either the oil phase was stirred into the water, or oil phase and water phase were combined without stirring. The mixture was then homogenized using a suitable homogenizer (e.g. Ultraturrax) for about 1-2 minutes.

Stabilizing polymers (e.g. carbomers) are preferably stirred into the emulsion as oil dispersion at temperatures of 50-60° C. The mixture is then briefly homogenized.

Addition of further ingredients (e.g. preservatives, active ingredients) was preferably carried out at 40° C. If the formulations were preserved with organic acids, the pH of the emulsions was adjusted to approximately 5.

These tests are intended to show that the inventive rhamnolipid derivatives have advantages in relation to emulsion stability in comparison to unmodified mono- or di-rhamnolipids and to short-chain mono- or di-rhamnolipid esters.

To test the storage stability of the emulsions, these were stored for three months at room temperature, 40° C. and 45° C. To test the low-temperature stability, moreover, they were stored for one month at −5° C., and three freeze-thaw cycles of 25° C./−15° C./25° C. were carried out. Considerable changes in the appearance or the consistency, and in particular oil or water separations, were weighted as criteria for instability.

Comparison of the inventive rhamnolipid derivatives as emulsifiers 3a-c and 4a and b versus the non-derivatized rhamnolipids according to Example 1 and 2 and also the non-inventively derivatized Examples 5a and b, in two lotions with different composition and polarity of the oil phase.

| Formulation 1 | 1-1 | 1-2 | 1-3 | 1-4 | 1-5 |
|---|---|---|---|---|---|
| Inventive rhamnolipid derivative according to Ex. 3a | 3.00% | — | — | — | — |
| Inventive rhamnolipid derivative according to Ex. 3b | — | 3.00% | — | — | — |
| Inventive rhamnolipid derivative according to Ex. 3c | — | — | 3.00% | — | — |
| Inventive rhamnolipid derivative according to Ex. 4a | — | — | — | 3.00% | — |

-continued

| | | | | | |
|---|---|---|---|---|---|
| Inventive rhamnolipid derivative according to Ex. 4b | — | — | — | — | 3.00% |
| Glyceryl Stearate | 0.50% | 0.50% | 0.50% | 0.50% | 0.50% |
| Stearic Acid | 0.50% | 0.50% | 0.50% | 0.50% | 0.50% |
| Caprylic/Capric Triglyceride | 5.50% | 5.50% | 5.50% | 5.50% | 5.50% |
| Ethylhexyl Palmitate | 6.30% | 6.30% | 6.30% | 6.30% | 6.30% |
| Water | to 100% | to 100% | to 100% | to 100% | to 100% |
| Glycerol | 3.00% | 3.00% | 3.00% | 3.00% | 3.00% |
| Carbomer¹ | 0.20% | 0.20% | 0.20% | 0.20% | 0.20% |
| Sodium Hydroxide (10% strength in water) | 0.60% | 0.60% | 0.60% | 0.60% | 0.60% |
| Phenoxyethanol; Ethylhexylglycerol² | 0.70% | 0.70% | 0.70% | 0.70% | 0.70% |
| Consistency after production | viscous | thinly | viscous | viscous | viscous |
| Stability | Stable | Stable | Stable | Stable | Stable |

| Formulation 1 | 1-6 | 1-7 | 1-8 | 1-9 |
|---|---|---|---|---|
| Noninventive, nonderivatized mono-rhamnolipid according to Ex. 2 | 3.00% | — | — | — |
| Noninventive, nonderivatized di-rhamnolipid according to Ex. 1 | — | 3.00% | — | — |
| Noninventive mono-rhamnolipid derivative according to Ex. 5b | — | — | 3.00% | — |
| Noninventive di-rhamnolipid derivative according to Ex. 5a | — | — | — | 3.00% |
| Glyceryl Stearate | 0.50% | 0.50% | 0.50% | 0.50% |
| Stearic Acid | 0.50% | 0.50% | 0.50% | 0.50% |
| Caprylic/Capric Triglyceride | 5.50% | 5.50% | 5.50% | 5.50% |
| Ethylhexyl Palmitate | 6.30% | 6.30% | 6.30% | 6.30% |
| Water | to 100% | to 100% | to 100% | to 100% |
| Glycerol | 3.00% | 3.00% | 3.00% | 3.00% |
| Carbomer³ | 0.20% | 0.20% | 0.20% | 0.20% |
| Sodium Hydroxide (10% strength in water) | 0.60% | 0.60% | 0.60% | 0.60% |
| Phenoxyethanol; Ethylhexylglycerol⁴ | 0.70% | 0.70% | 0.70% | 0.70% |
| Consistency after production | pasty | pasty | pasty | pasty |
| Stability | Phase separation after 1 day at RT | Phase separation after 1 day at RT | Phase separation after 3 days at RT | Phase separation after 3 days at RT |

| Formulation 2 | 2-1 | 2-2 | 2-3 | 2-4 | 2-5 |
|---|---|---|---|---|---|
| Inventive rhamnolipid derivative according to Ex. 3a | 3.00% | — | — | — | — |
| Inventive rhamnolipid derivative according to Ex. 3b | — | 3.00% | — | — | — |
| Inventive rhamnolipid derivative according to Ex. 3c | — | — | 3.00% | — | — |
| Inventive rhamnolipid derivative according to Ex. 4a | — | — | — | 3.00% | — |
| Inventive rhamnolipid derivative according to Ex. 4b | — | — | — | — | 3.00% |
| Glyceryl Stearate | 0.50% | 0.50% | 0.50% | 0.50% | 0.50% |
| Stearic Acid | 0.50% | 0.50% | 0.50% | 0.50% | 0.50% |
| Ethylhexyl Palmitate | 6.30% | 6.30% | 6.30% | 6.30% | 6.30% |
| Paraffinum Perliquidum | 5.50% | 5.50% | 5.50% | 5.50% | 5.50% |
| Water | to 100% | to 100% | to 100% | to 100% | to 100% |
| Glycerol | 3.00% | 3.00% | 3.00% | 3.00% | 3.00% |
| Carbomer¹ | 0.20% | 0.20% | 0.20% | 0.20% | 0.20% |
| Sodium Hydroxide (10% strength in water) | 0.60% | 0.60% | 0.60% | 0.60% | 0.60% |
| Phenoxyethanol; Ethylhexylglycerol² | 0.70% | 0.70% | 0.70% | 0.70% | 0.70% |
| Consistency after production | viscous | thinly | viscous | viscous | viscous |
| Stability | Stable | Stable | Stable | Stable | Stable |

| Formulation 2 | 2-6 | 2-7 | 2-8 | 2-9 |
|---|---|---|---|---|
| Noninventive, nonderivatized mono-rhamnolipid according to Ex. 2 | 3.00% | — | — | — |
| Noninventive, nonderivatized di-rhamnolipid according to Ex. 1 | — | 3.00% | — | — |
| Noninventive mono-rhamnolipid derivative according to Ex. 5b | — | — | 3.00% | — |
| Noninventive di-rhamnolipid derivative according to Ex. 5a | — | — | — | 3.00% |
| Glyceryl Stearate | 0.50% | 0.50% | 0.50% | 0.50% |
| Stearic Acid | 0.50% | 0.50% | 0.50% | 0.50% |
| Ethylhexyl Palmitate | 6.30% | 6.30% | 6.30% | 6.30% |
| Paraffinum Perliquidum | 5.50% | 5.50% | 5.50% | 5.50% |
| Water | to 100% | to 100% | to 100% | to 100% |
| Glycerol | 3.00% | 3.00% | 3.00% | 3.00% |
| Carbomer¹ | 0.20% | 0.20% | 0.20% | 0.20% |
| Sodium Hydroxide (10% strength in water) | 0.60% | 0.60% | 0.60% | 0.60% |
| Phenoxyethanol; Ethylhexylglycerol² | 0.70% | 0.70% | 0.70% | 0.70% |
| Consistency after production | pasty | pasty | pasty | pasty |
| Stability | Phase separation after 1 day at RT | Phase separation after 1 day at RT | Phase separation after 5 days at RT | Phase separation after 5 days at RT |

While the formulations with the inventive emulsifiers 3a-c and 4a and b each lead to a storage-stable lotion, each of the formulations with the non-inventive comparative emulsifiers from Examples 1, 2, 5a and 5b shows an initially excessively high viscosity and significant weaknesses in the storage-stability of the emulsion.

[1] TEGO® Carbomer 141 (Evonik Nutrition & Care GmbH)
[2] Euxyl PE 9010 (Schülke & Mayr GmbH)
[3] TEGO® Carbomer 141 (Evonik Nutrition & Care GmbH)
[4] Euxyl PE 9010 (Schülke & Mayr GmbH)

Formulation Examples

These examples are intended to show that the inventive rhamnolipid derivatives can be used in a large number of cosmetic formulations as emulsifiers.

Moreover, with the help of the inventive rhamnolipid derivatives, it is possible to stably incorporate pigments or solids into emulsion preparations.

Furthermore, the examples show good compatibility with typical coemulsifiers, oils, thickeners and stabilizers, and also good compatibility with emulsion-burdening ingredients such as UV filters, active antimicrobial ingredients or active cosmetic ingredients.

| Lotions with low emulsifier content | | | | |
|---|---|---|---|---|
| Formulation | 3-1 | 3-2 | 4-1 | 4-2 |
| Inventive rhamnolipid derivative according to Ex. 4a | 1.00% | 0.50% | 1.00% | 0.50% |
| Cetearyl Glucoside[5] | — | 0.50% | — | — |
| Polyglyceryl-6 Stearate; Polyglyceryl-6 Behenate[6] | — | — | — | 1.00% |
| Glyceryl Stearate | 0.50% | 0.50% | 0.50% | 0.50% |
| Stearic Acid | 0.50% | 0.50% | 0.50% | 0.50% |
| Caprylic/Capric Triglyceride | 6.50% | 6.50% | — | — |
| Ethylhexyl Palmitate | 8.10% | 8.10% | 8.10% | 8.10% |
| Paraffinum Perliquidum | — | — | 6.50% | 6.50% |
| Water | to 100% | to 100% | to 100% | to 100% |
| Glycerol | 3.00% | 3.00% | 3.00% | 3.00% |
| Carbomer[1] | 0.20% | 0.20% | 0.20% | 0.20% |
| Sodium Hydroxide (10% strength in water) | 0.60% | 0.60% | 0.60% | 0.60% |
| Phenoxyethanol; Ethylhexylglycerol[2] | 0.70% | 0.70% | 0.70% | 0.70% |

| Serum | | | | |
|---|---|---|---|---|
| Formulation | 5-1 | 5-2 | 5-3 | 5-4 |
| Inventive rhamnolipid derivative according to Ex. 3a | 2.00% | 1.00% | — | — |
| Inventive rhamnolipid derivative according to Ex. 3c | — | — | 2.00% | 1.00% |
| Sorbitan Laurate; Polyglyceryl-4 Laurate; Dilauryl Citrate[7] | — | 1.00% | — | 1.00% |
| Ethylhexyl Stearate | 7.00% | 7.00% | 7.00% | 7.00% |
| Octyldodecanol | 4.00% | 4.00% | 4.00% | 4.00% |
| Caprylic/Capric Triglyceride | 2.00% | 2.00% | 2.00% | 2.00% |
| Carbomer[8] | 0.15% | 0.15% | 0.15% | 0.15% |
| Carbomer[1] | 0.15% | 0.15% | 0.15% | 0.15% |
| Xanthan Gum[9] | 0.10% | 0.10% | 0.10% | 0.10% |
| Hydrolysed Hyaluronic Acid[10] | 0.10% | 0.10% | 0.10% | 0.10% |
| Ceteareth-25; Glycerol; Cetyl Alcohol; Behenic Acid; Cholesterol; Ceramide EOS; Ceramide NP; Ceramide NS; Ceramide AP; Caprooyl Phytosphingosine; Caprooyl Sphingosine[11] | 1.00% | 1.00% | 1.00% | 1.00% |
| Glycerol | 3.00% | 3.00% | 3.00% | 3.00% |
| Water | to 100% | to 100% | to 100% | to 100% |
| Sodium Hydroxide (10% strength in water) | 0.90% | 0.90% | 0.90% | 0.90% |
| Caprooyl Phytosphingosine[12] | 0.10% | 0.10% | 0.10% | 0.10% |
| Pentylene Glycol | 1.40% | 1.40% | 1.40% | 1.40% |
| Phenoxyethanol; Caprylyl Glycol[13] | 1.00% | 1.00% | 1.00% | 1.00% |

| O/W sunscreen lotion, SPF 30 | | | | |
|---|---|---|---|---|
| Formulation | 6-1 | 6-2 | 6-3 | 6-4 |
| Inventive rhamnolipid derivative according to Ex. 4a | 3.00% | 1.00% | — | — |
| Inventive rhamnolipid derivative according to Ex. 4b | — | — | 3.00% | 1.00% |
| Cetearyl Glucoside[3] | — | 1.00% | — | 1.00% |
| Phenoxyethyl Caprylate[14] | 6.10% | 6.10% | 6.10% | 6.10% |
| Cetearyl Alcohol | 1.00% | 1.00% | 1.00% | 1.00% |
| Octocrylene | 4.80% | 4.80% | 4.80% | 4.80% |
| Ethylhexyl Triazone | 4.50% | 4.50% | 4.50% | 4.50% |
| Butyl Methoxydibenzoylmethane | 2.50% | 2.50% | 2.50% | 2.50% |
| Bis-Ethylhexyloxyphenol Methoxyphenyl Triazine[15] | 5.50% | 5.50% | 5.50% | 5.50% |
| Tocopheryl Acetate | 0.50% | 0.50% | 0.50% | 0.50% |
| Glycerol | 2.00% | 2.00% | 2.00% | 2.00% |
| Water | to 100% | to 100% | to 100% | to 100% |
| Acrylates/C10-30 Alkyl Acrylate Crosspolymer[16] | 0.10% | 0.10% | 0.10% | 0.10% |
| Sodium Hydroxide (10% strength in water) | 0.30% | 0.30% | 0.30% | 0.30% |
| Dipropylene Glycol; Methylparaben; Ethylparaben; Aqua; Methylisothiazolinone[17] | 0.80% | 0.80% | 0.80% | 0.80% |

| Lotion based on natural ingredients | | | | |
|---|---|---|---|---|
| Formulation | 7-1 | 7-2 | 7-3 | 7-4 |
| Inventive rhamnolipid derivative according to Ex. 4a | 2.50% | 1.50% | — | — |
| Inventive rhamnolipid derivative according to Ex. 4b | — | — | 2.50% | 1.50% |
| Polyglyceryl-3 Dicitrate/Stearate[18] | — | 1.00% | — | 1.00% |
| Isopropyl Palmitate | 5.00% | 5.00% | 5.00% | 5.00% |
| *Prunus Amygdalus Dulcis* (Sweet Almond) Oil | 5.00% | 5.00% | 5.00% | 5.00% |
| Water | to 100% | to 100% | to 100% | to 100% |
| Glycerol | 3.00% | 3.00% | 3.00% | 3.00% |
| Xanthan Gum[7] | 0.50% | 0.50% | 0.50% | 0.50% |
| Sodium Hydroxide (10% strength in water) | 0.20% | 0.20% | 0.20% | 0.20% |
| Benzyl Alcohol; glycerol; Benzoic Acid; Sorbic Acid[19] | 0.80% | 0.80% | 0.80% | 0.80% |

| Light O/W lotion produced at low temperature | | |
|---|---|---|
| Formulation | 8-1 | 8-2 |
| Inventive rhamnolipid derivative according to Ex. 3a | 2.50% | 1.50% |
| Sorbitan Laurate; Polyglyceryl-4 Laurate; Dilauryl Citrate[5] | — | 1.00% |
| Ethylhexyl Palmitate | 1.10% | 1.10% |
| Isohexadecane | 5.50% | 5.50% |
| Cyclopentasiloxane | 5.00% | 5.00% |
| Cellulose[20] | 1.00% | 1.00% |
| Carbomer[6] | 0.15% | 0.15% |
| Carbomer[1] | 0.15% | 0.15% |
| Xanthan Gum | 0.10% | 0.10% |
| Glycerol | 3.00% | 3.00% |
| Water | to 100% | to 100% |
| Sodium Hydroxide (10% strength in water) | 0.90% | 0.90% |

| | | |
|---|---|---|
| Phenoxyethanol; Ethylhexylglycerol[2] | 0.70% | 0.70% |

O/W Baby Lotion

| Formulation | 9-1 | 9-2 |
|---|---|---|
| Inventive rhamnolipid derivative according to Ex. 3a | 3.00% | 2.00% |
| Polyglyceryl-3 Methylglucose Distearate[21] | — | 0.50% |
| Stearyl Alcohol | 1.00% | 1.00% |
| Isopropyl Palmitate | 7.30% | 7.30% |
| Triisostearin | 4.00% | 4.00% |
| Squalane | 1.00% | 1.00% |
| Dimethicone[22] | 0.50% | 0.50% |
| Water | to 100% | to 100% |
| Glycerol | 3.00% | 3.00% |
| Carbomer[1] | 0.20% | 0.20% |
| Sodium Hydroxide (10% strength in water) | 0.60% | 0.60% |
| Sodium Lactate; Sodium PCA; Glycine; Fructose; Urea; Niacinamide; Inositol; Sodium Benzoate; Lactic Acid[23] | 3.00% | 3.00% |
| Phenoxyethanol; Caprylyl Glycol[11] | 1.00% | 1.00% |

Solution for impregnation of wet wipes for baby care

| Formulation | 10-1 | 10-2 | 10-3 | 10-4 |
|---|---|---|---|---|
| Inventive rhamnolipid derivative according to Ex. 4a | 1.50% | 1.00% | — | — |
| Inventive rhamnolipid derivative according to Ex. 3b | — | — | 2.50% | 1.50% |
| Cetearyl Glucoside[3] | — | 0.50% | — | 0.50% |
| Polyglyceryl-3 Caprate[24] | 0.50% | 0.50% | 0.50% | 0.50% |
| C12-15 Alkyl Benzoate | 5.00% | 5.00% | 5.00% | 5.00% |
| Mineral Oil | 5.00% | 5.00% | 5.00% | 5.00% |
| Gellan Gum[25] | 0.03% | 0.03% | 0.03% | 0.03% |
| Water | to 100% | to 100% | to 100% | to 100% |
| Glycerol | 2.00% | 2.00% | 2.00% | 2.00% |
| Acrylates/C10-30 Alkyl Acrylate Crosspolymer[14] | 0.05% | 0.05% | 0.05% | 0.05% |
| Sodium Hydroxide (10% strength in water) | 0.15% | 0.15% | 0.15% | 0.15% |
| Phenoxyethanol; Ethylhexylglycerol[2] | 0.70% | 0.70% | 0.70% | 0.70% |

O/W foundation for a natural skin feel

| Formulation | 11-1 | 11-2 | 11-3 | 11-4 |
|---|---|---|---|---|
| Inventive rhamnolipid derivative according to Ex. 3a | 5.00% | 3.00% | 5.00% | 3.00% |
| Polyglyceryl-6 Stearate (and) Polyglyceryl-6 Behenate[4] | — | 1.50% | — | 1.50% |
| Cetearyl Alcohol | 1.50% | 1.50% | 1.50% | 1.50% |
| Glyceryl Stearate | 1.00% | 1.00% | 1.00% | 1.00% |
| Myristyl Myristate[26] | 1.00% | 1.00% | 1.00% | 1.00% |
| C12-15 Alkyl Benzoate | 3.00% | 3.00% | 3.00% | 3.00% |
| Diethylhexyl Carbonate[27] | 2.00% | 2.00% | 2.00% | 2.00% |
| Cyclopentasiloxane (and) Dimethicone Crosspolymer[28] | 2.00% | 2.00% | 2.00% | 2.00% |
| Ethylhexyl Methoxycinnamate | 8.00% | 8.00% | 8.00% | 8.00% |
| Ethylhexyl Salicylate | 5.00% | 5.00% | 5.00% | 5.00% |
| Diethylamino Hydroxybenzoyl Hexyl Benzoate[29] | 3.00% | 3.00% | 3.00% | 3.00% |
| Bis-Ethylhexyloxyphenol Methoxyphenyl Triazine[13] | 3.00% | 3.00% | 3.00% | 3.00% |
| Water | to 100% | to 100% | to 100% | to 100% |
| Glycerol | 1.00% | 1.00% | 1.00% | 1.00% |
| Xanthan Gum | 0.15% | 0.15% | 0.15% | 0.15% |
| Titanium Dioxide; CI 77891 | 8.00% | 8.00% | 8.00% | 8.00% |
| CI 77492; Aqua; Glycerol; Xanthan Gum; Sodium Citrate[30] | 1.70% | 1.70% | 1.70% | 1.70% |
| CI 77491; Aqua; Glycerol; Xanthan Gum; Sodium Citrate[31] | 0.40% | 0.40% | 0.40% | 0.40% |
| CI 77499; Aqua; Glycerol; Xanthan Gum; Sodium Citrate[32] | 0.10% | 0.10% | 0.10% | 0.10% |
| Glycerol | 2.00% | 2.00% | 2.00% | 2.00% |
| Propylene Glycol | 3.00% | 3.00% | 3.00% | 3.00% |
| Nylon-12 | 2.00% | 2.00% | — | — |
| Cellulose[18] | — | — | 2.00% | 2.00% |
| Phenoxyethanol; Ethylhexylglycerol[2] | 0.70% | 0.70% | 0.70% | 0.70% |

O/W lotion for make-up removal with silky skin feel

| Formulation | 12-1 | 12-2 |
|---|---|---|
| Inventive rhamnolipid derivative according to Ex. 3a | 3.00% | 2.00% |
| Bis-PEG/PPG-20/5 PEG/PPG-20/5 Dimethicone: Methoxy PEG/PPG-25/4 Dimethicone; Caprylic/Capric Triglyceride[33] | — | 1.00% |
| Decyl Cocoate[34] | 7.00% | 7.00% |
| Paraffinum Perliquidum | 7.00% | 7.00% |
| Acrylates/C10-30 Alkyl Acrylate Crosspolymer[14] | 0.15% | 0.15% |
| Glycerol | 3.00% | 3.00% |
| Water | to 100% | to 100% |
| Sodium Hydroxide (10% strength in water) | 0.45% | 0.45% |
| Alcohol | 3.00% | 3.00% |
| Phenoxyethanol; Caprylyl Glycol[11] | 1.00% | 1.00% |

Natural oil-releasing cream

| Formulation | 13-1 | 13-2 | 14-1 | 14-2 |
|---|---|---|---|---|
| Inventive rhamnolipid derivative according to Ex. 4a | 4.00% | 2.00% | 4.00% | 2.00% |
| Polyglyceryl-3 Distearate; Glyceryl Stearate Citrate[35] | — | 1.00% | — | — |

-continued

| | | | | |
|---|---|---|---|---|
| Polyglyceryl-6 Stearate; Polyglyceryl-6 Behenate | — | — | — | 1.00% |
| Decyl Cocoate[32] | 72.00% | 72.00% | — | — |
| *Helianthus Annuus* (Sunflower) Seed Oil | — | — | 70.0% | 70.0% |
| Glycerol | 2.00% | 2.00% | 2.00% | 2.00% |
| Water | to 100% | to 100% | to 100% | to 100% |
| Benzyl Alcohol; Glycerol; Benzoic Acid; Sorbic Acid[17] | 1.00% | 1.00% | 1.00% | 1.00% |
| Citric Acid (10% aq.) | q.s. | q.s. | q.s. | q.s. |

| Low-viscosity W/O lotion | | | | |
|---|---|---|---|---|
| Formulation | 15-1 | 15-2 | 16-1 | 16-2 |
| Polyglyceryl-4 Diisostearate/ Polyhydroxystearate/ Sebacate[36] | 2.50% | 2.50% | — | — |
| PEG/PPG-10/1 Dimethicone[37] | — | — | 1.50% | 1.50% |
| Inventive rhamnolipid derivative according to Ex. 4a | 0.50% | 0.20% | 0.50% | 0.20% |
| Di-Rhamnolipid | — | 0.20% | — | 0.20% |
| Hydrogenated Castor Oil | 0.20% | 0.20% | 0.20% | 0.20% |
| Isopropyl Palmitate | 10.00% | 10.00% | — | — |
| *Prunus Amygdalus Dulcis* (Sweet Almond) Oil | 8.00% | 8.00% | — | — |
| Diethylhexyl Carbonate[25] | 7.00% | 7.00% | 10.00% | 10.00% |
| Ethylhexyl Palmitate | — | — | 8.00% | 8.00% |
| Dimethicone (5 mPas) | — | — | 5.00% | 5.00% |
| Glycerol | 3.00% | 3.00% | 2.00% | 2.00% |
| Water | to 100% | to 100% | to 100% | to 100% |
| Magnesium Sulfate Heptahydrate | 1.50% | 1.50% | — | — |
| Sodium Chloride | — | — | 0.80% | 0.80% |
| Benzyl Alcohol; Glycerol; Benzoic Acid; Sorbic Acid[17] | 1.00% | 1.00% | 1.00% | 1.00% |
| Citric Acid (10% aq.) | q.s. | q.s. | q.s. | q.s. |

The invention claimed is:

1. A dispersion, containing
A) a at least one rhamnolipid derivative,
B) at least one cosmetic oil, and
C) water,
wherein the at least one rhamnolipid derivative is selected from the group consisting of rhamnolipid ester of the general formula (I) and rhamnolipid amide of the general formula (II):

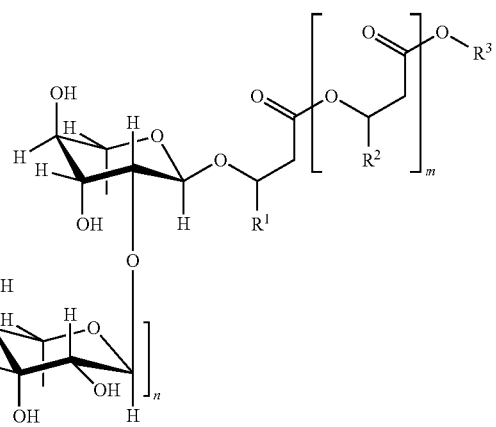

general formula (I),
wherein
m=2, 1 or 0,
n=1 or 0,
and when n=0, the $C_2$ of the sugar is substituted with an OH group,
$R^1$=organic radical having from 5 to 13 carbon atoms,
$R^2$=independently of one another, identical or different, organic radical having from 5 to 13 carbon atoms, and
$R^3$=aliphatic radical having from 10 to 32 carbon atoms;

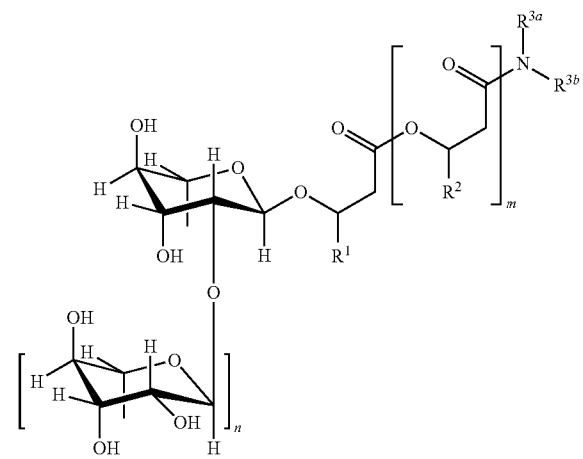

general formula (II),
wherein
m=2, 1 or 0,
n=1 or 0,
and when n=0, the $C_2$ of the sugar is substituted with an OH group,
$R^1$=organic radical having from 5 to 13 carbon atoms,
$R^2$=independently of one another, identical or different, organic radical having from 5 to 13 carbon atoms,
$R^{3a}$=organic radical having from 10 to 22 carbon atoms, and $R^{3b}$=organic radical having from 10 to 22 carbon atoms,
wherein the sum of the carbon atoms contained in $R^{3a}$ and $R^{3b}$ is 20 to 44; and
wherein the at least one cosmetic oil has an interfacial tension with respect to water of >5 mN/m.

2. The dispersion according to claim 1, wherein the dispersion is an emulsion.

3. The dispersion according to claim 1, wherein the dispersion contains
A) from 0.5 wt % to 7.0 wt % of the at least one rhamnolipid derivative,
B) from 10.0 wt % to 50.0 wt % of at least one cosmetic oil, and
C) from 50.0 wt % to 90.0 wt % of water.

4. The dispersion according to claim 1, wherein it contains
A) in an amount of from 0.1 wt % to 10.0 wt %,
B) in an amount of from 5.0 wt % to 79.9 wt %,
C) in an amount of from 20.0 wt % to 94.9 wt %,
wherein the percentages by weight refer to the total dispersion.

5. The dispersion according to claim 1, wherein, in the rhamnolipid ester present, $R^3$ is selected from the group of the $R^3$ radicals directly derived from $R^3OH$=natural fatty alcohol.

6. The dispersion according to claim 1, wherein, in the rhamnolipid ester present, $R^3$ is selected from branched or linear alkyl radicals.

7. The dispersion according to claim 1, wherein, in the rhamnolipid ester present, $R^3$ is selected from the group consisting of lauryl, myristyl, palmityl, stearyl, arachidyl and behenyl radicals.

8. The dispersion according to claim 1, wherein, in the rhamnolipid amide present, $R^{3a}$ is selected from the group of the alkyl radicals comprising groups.

9. The dispersion according to claim 1, wherein, in the rhamnolipid amide present, $R^{3a}$ is selected from the group consisting of

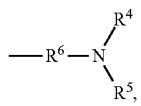

where
$R^4$ and $R^5$=independently of one another, identical or different alkyl radical with 1 to 6, carbon atom(s),
$R^6$=an alkylene group with 1 to 6, carbon atoms,
and

wherein
$R^7$=an alkylene group with 10 to 22 carbon atoms,
Z=H, OH, $OR^8$, where
$R^8$=alkyl radical with 1 to 6 carbon atoms.

10. The dispersion according to claim 1, wherein, in the rhamnolipid amide present, the radical —$NR^{3a}R^{3b}$ is derived from an amine $NHR^{3a}R^{3b}$, selected from amino acids and peptides.

11. The dispersion according to claim 1, wherein in formula (I)
m=1 or 0,
n=1,
wherein in formula (II),
m=1 or 0,
n=1,
wherein the sum of the carbon atoms contained in $R^{3a}$ and $R^{3b}$ is from 20 to 24.

12. The dispersion according to claim 1, wherein for formula (I)
m=1 or 0,
n=1,
$R^1$=is selected from the group consisting of pentenyl, heptenyl, nonenyl, undecenyl and tridecenyl,
$R^2$=is selected from the group consisting of pentenyl, heptenyl, nonenyl, undecenyl and tridecenyl,
and
wherein for formula (II)
m=1 or 0,
n=1,
$R^1$=is selected from the group consisting of pentenyl, heptenyl, nonenyl, undecenyl and tridecenyl,
$R^2$=is selected from the group consisting of pentenyl, heptenyl, nonenyl, undecenyl and tridecenyl.

13. The dispersion according to claim 1, wherein for formula (I)
m=1 or 0,
n=1,
$R^1$=is selected from the group consisting of pentenyl, heptenyl, nonenyl, undecenyl, tridecenyl and $(CH_2)_o$—$CH_3$ where o=4 to 12,
$R^2$=is selected from the group consisting of pentenyl, heptenyl, nonenyl, undecenyl, tridecenyl, and $(CH_2)_o$—$CH_3$ where o=4 to 12, and
$R^3$=aliphatic radical having from 10 to 22 carbon atoms;
and
wherein for formula (II)
m=1 or 0,
n=1,
$R^1$=is selected from the group consisting of pentenyl, heptenyl, nonenyl, undecenyl, tridecenyl, and $(CH_2)_o$—$CH_3$ where o=4 to 12,
$R^2$=is selected from the group consisting of pentenyl, heptenyl, nonenyl, undecenyl, tridecenyl, and $(CH_2)_o$—$CH_3$ where o=4 to 12,
$R^{3a}$=organic radical having from 10 to 22 carbon atoms,
wherein the sum of the carbon atoms contained in $R^{3a}$ and $R^{3b}$ is from to 22.

14. The dispersion according to claim 3, wherein it contains
A) in an amount of from 1.0 wt % to 5.0 wt %,
B) in an amount of from 12.0 wt % to 35.0 wt %,
C) in an amount of from 65.0 wt % to 88.0 wt %, wherein the percentages by weight refer to the total dispersion.

15. The dispersion according to claim 1, wherein, in the rhamnolipid A amide present, $R^{3a}$ is selected from the group of the alkyl radicals comprising amine groups.

16. A dispersion, containing at least A) at least one rhamnolipid derivative selected from the group consisting of rhamnolipid ester of the general formula (I) and rhamnolipid amide of the general formula (II):

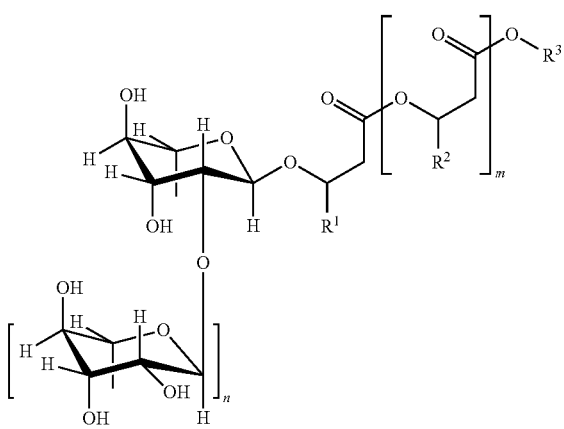

general formula (I),
wherein
m=1,
n=1 or 0,
and when n=0, the C2 of the sugar is substituted with an OH group,
$R^1$=organic radical having from 5 to 13 carbon atoms,
$R^2$=independently of one another, identical or different, organic radical having from 5 to 13 carbon atoms, and
$R^3$=aliphatic radical having from 10 to 32 carbon atoms;

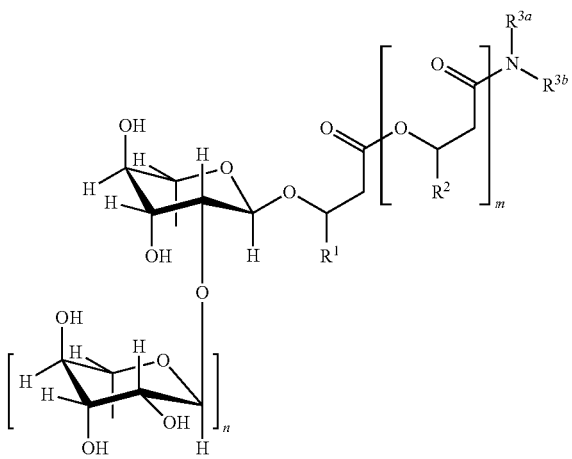

general formula (II),
wherein
m=1,
n=1 or 0,
and when n=0, the C2 of the sugar is substituted with an OH group,
$R^1$=organic radical having from 5 to 13 carbon atoms,
$R^2$=independently of one another, identical or different, organic radical having from 5 to 13 carbon atoms,
$R^{3a}$=organic radical having from 10 to 32 carbon atoms, and $R^{3b}$=organic radical having from 10 to 32 carbon atoms,
wherein the sum of the carbon atoms contained in $R^{3a}$ and $R^{3b}$ is 20 to 44.

17. The dispersion according to claim 16, wherein the dispersion is an emulsion.

18. The dispersion according to claim 16, wherein the dispersion contains

A) the at least one rhamnolipid derivative,
B) at least one cosmetic oil, and
C) water.

19. The dispersion according to claim 18, wherein it contains

A) in an amount of from 0.1 wt % to 10.0 wt %,
B) in an amount of from 5.0 wt % to 79.9 wt %,
C) in an amount of from 20.0 wt % to 94.9 wt %, wherein the percentages by weight refer to the total dispersion.

20. The dispersion according to claim 16, wherein, in the rhamnolipid ester present, $R^3$ is selected from the group of the $R^3$ radicals directly derived from $R^3$OH=natural fatty alcohol.

21. The dispersion according to claim 16, wherein, in the rhamnolipid ester present, $R^3$ is selected from branched or linear alkyl radicals.

22. The dispersion according to claim 16, wherein, in the rhamnolipid ester present, $R^3$ is selected from the group consisting of lauryl, myristyl, palmityl, stearyl, arachidyl and behenyl radicals.

23. A method of emulsifying and/or dispersing, comprising:
preparing an emulsion and/or dispersion with
A) at least one rhamnolipid derivative selected from the group consisting of a rhamnolipid ester of the general formula (I) and a rhamnolipid amide of the general formula (II):

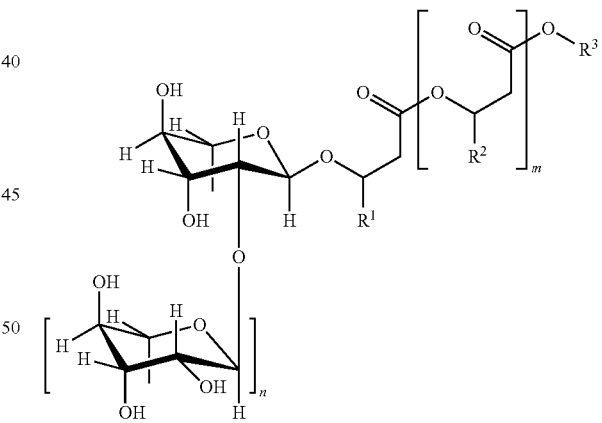

general formula (I),
wherein
m=2, 1 or 0,
n=1 or 0,
and when n=0, the $C_2$ of the sugar is substituted with an OH group,
$R^1$=organic radical having from 5 to 13 carbon atoms,
$R^2$=independently of one another, identical or different, organic radical having from 5 to 13 carbon atoms, and
$R^3$=aliphatic radical having from 10 to 32 carbon atoms;

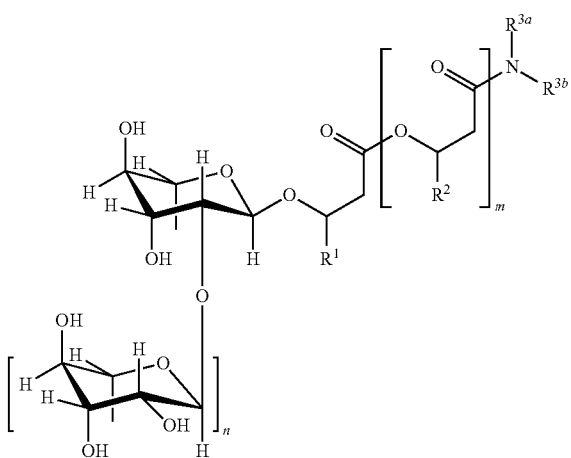

general formula (II), wherein m=2, 1 or 0, n=1 or 0, and when n=0, the C2 of the sugar is substituted with an OH group, $R^1$=organic radical having from 5 to 13 carbon atoms, $R^2$=independently of one another, identical or different, organic radical having from 5 to 13 carbon atoms, $R^{3a}$=organic radical having from 10 to 22 carbon atoms, and $R^{3b}$=organic radical having from 10 to 22 carbon atoms, wherein the sum of the carbon atoms contained in $R^{3a}$ and $R^{3b}$ is 20 to 44

B) at least one cosmetic oil; and

C) water.

* * * * *